United States Patent
Kapre

(10) Patent No.: US 9,700,615 B2
(45) Date of Patent: Jul. 11, 2017

(54) ADJUVANT FORMULATIONS AND METHODS

(71) Applicant: Serum Institute of India Pvt. Ltd., India Pune (IN)

(72) Inventor: Subhash V. Kapre, Bellevue, WA (US)

(73) Assignee: Serum Institute of India Pvt. Ltd., Pune (IN)

( * ) Notice: Subject to any disclaimer, the term of this patent is extended or adjusted under 35 U.S.C. 154(b) by 0 days.

(21) Appl. No.: 14/383,995

(22) PCT Filed: May 13, 2013

(86) PCT No.: PCT/IB2013/053890
§ 371 (c)(1),
(2) Date: Sep. 9, 2014

(87) PCT Pub. No.: WO2013/171661
PCT Pub. Date: Nov. 21, 2013

(65) Prior Publication Data
US 2015/0056250 A1 Feb. 26, 2015

Related U.S. Application Data

(60) Provisional application No. 61/647,390, filed on May 15, 2012.

(51) Int. Cl.
*A61K 39/39* (2006.01)
*A61K 39/13* (2006.01)
*C07K 14/00* (2006.01)
*C12N 7/00* (2006.01)
*C07K 14/315* (2006.01)
*A61K 39/00* (2006.01)

(52) U.S. Cl.
CPC ............. *A61K 39/39* (2013.01); *A61K 39/13* (2013.01); *C07K 14/00* (2013.01); *C07K 14/3156* (2013.01); *C12N 7/00* (2013.01); *A61K 2039/55516* (2013.01); *C12N 2770/32634* (2013.01); *C12N 2770/32671* (2013.01)

(58) Field of Classification Search
None
See application file for complete search history.

(56) References Cited

U.S. PATENT DOCUMENTS 8,173,135 B2* 5/2012 Lee ................... A61K 39/385
424/184.1
2012/0076817 A1 3/2012 Lee et al.

FOREIGN PATENT DOCUMENTS

WO WO 2010/120921 10/2010
WO WO 2011/151760 12/2011

OTHER PUBLICATIONS

Sharma et al. A simple and rapid method for quantifying 2-phenoxyethanol (2-PE) in Diphtheria, Tetanus and w-Pertussis (DTwP) vaccine. Biologicals. Jan. 2008;36(1):61-3. Epub Aug. 28, 2007.*
Recommendations and Reports by CDC. Prevention of Pneumococcal Disease: Recommendations of the Advisory Committee on Immunization Practices (ACIP). Apr. 4, 1997 / 46(RR-08);1-24.*
Rajam et al. Pneumococcal Surface Adhesin A (PsaA): A Review. Critical Reviews in Microbiology, 34:131-142, 2008.*
PCT Search and Patentability Report for PCT/IB13/53890, dated Dec. 13, 2013.

* cited by examiner

*Primary Examiner* — Nick Zou
(74) *Attorney, Agent, or Firm* — Perkins Coie LLP

(57) ABSTRACT

The present invention is directed to methods for administering antigenic material to a patient as a vaccine against an infection comprising providing both an antigenic material specific to the desired immunological response desired plus an adjuvant comprised of a peptide of a sequence derived from the sequence of pneumococcal surface adhesin A protein (PsaA). Preferably the peptide comprises a sequences derived from one or more sequences of PsaA that contain the epitope regions or contiguous amino acids of SEQ ID NOs 1 or 2. The invention is also directed to vaccine compositions containing adjuvant of the invention and also adjuvant compositions of the invention.

22 Claims, No Drawings

ADJUVANT FORMULATIONS AND METHODS

REFERENCE TO RELATED APPLICATIONS

This Application claims priority to U.S. Provisional Application No. 61/647,390 of the same title and filed May 15, 2012, the entirety of which is hereby incorporated by reference.

SEQUENCE LISTING

The instant application contains a Sequence Listing which has been submitted in ASCII format via EFS-Web and is hereby incorporated by reference in its entirety. Said ASCII copy, created on May 8, 2013, is named 3036.003.PCT_SL.txt and is 3,640 bytes in size.

BACKGROUND

1. Field of the Invention

The invention is directed to peptides as adjuvants in vaccine production and methods of using peptides to increase the immune response to vaccine formulations. In particular, the invention is directed to methods of producing vaccines having smaller dosing of an antigenic material and/or greater immune response while maintaining a high level of efficacy.

2. Description of the Background

Vaccines have been used for the last 216 years to help prevent the spread of infectious diseases within a population of people. Since Edward Jenner's 1796 discovery that cowpox material created human immunity to smallpox, advances in awareness and technologies have seen the practice of vaccination become commonplace for a wide variety of infectious agents. Over the last fifty years, vaccination has transformed lives in both developed and undeveloped countries alike, contributing to the eradication of smallpox and large reductions of previously common diseases such as measles, typhoid and polio.

While advances in vaccinations have prevented an uncountable number of deaths from disease, it is estimated that 1.2 million people die needlessly each year because they do not receive vaccinations for tetanus, whooping cough, measles, tuberculosis, diphtheria and polio-vaccinations that have been widely available in developed countries since at least the 1960's. At least an additional 2 million deaths per year could be prevented by the full utilization of vaccines against *Haemophilus influenzae* type B (Hib) and hepatitis B.

The discrepancies of the use of existing vaccines can be attributed to the fact that many existing vaccines have not been affordable for developing countries. More than ten years after the universal introduction of the Hib vaccine, which protects against ear infections, meningitis, pneumonia and sepsis, fewer than 10% of children in the poorest 75% of countries were regularly receiving it as part of their immunization package due to the inability of governments and/or health care infrastructures to pay for the per dose immunization cost.

Between 1980 and 2009, the world's population more than doubled. However, during that time, the number of diphtheria cases dropped by 99%, polio cases by 97% and measles and pertussis cases by 95% each. These sharp decreases coincided with the widespread introduction of affordable vaccines into the marketplace. By increasing the affordability and access to vaccines and immunizations throughout the developed and underdeveloped world, within the next 20 years these diseases can be effectively eradicated.

In the case of poliomyelitis (polio); a highly infectious incurable viral disease that attacks the nervous system and causes permanent paralysis, prevention through vaccination is the only protection for a population. There are currently two types of polio vaccines available. Oral polio vaccine (OPV) and inactivated polio vaccine (IPV), delivered through injection. Although oral polio vaccine has been a valuable tool against the spread of the disease and is very inexpensive ($0.12-$0.20 per dose), OPV has two main drawbacks: the attenuated virus in OPV can mutate into a vaccine derived poliovirus (known as VDVP) that can cause polio infections in a population and on other, rare occasions, can result in vaccine-associated paralytic polio. On the other hand, currently available inactivated polio vaccines are more safe and effective, but cost nearly $3 per dose; too much for many underdeveloped countries to afford.

As vaccination will be needed for many years and perhaps decades after the spread of polio is eradicated, and since VDPV's will continue to occur until all populations switch to IPV, it is imperative that the price of IPV's are reduced so that underdeveloped countries can afford their widespread use. Several strategies have been proposed including the use of adjuvants to increase the body's immune response and/or needle-free delivery mechanisms that require smaller amounts of antigenic material per dose.

Each day, the human body is attacked by bacteria, viruses or other infectious agents. When a person becomes infected with a disease causing agent, the body's built-in immune system attempts to defend against the foreign agent. When the body successfully defends itself, immunity against the infectious agent is the result. When the body's natural defenses fail to quell the attack, an infection often results. In the natural process of developing immunity, B cells produced by the body produce substances known as antibodies that act against the specific infectious agent and create a "log" of this experience that can be called upon for protection when exposed to the same infectious agent again months, years or even decades later. Any subsequent time the person encounters that specific infectious agent; the circulating antibodies quickly recognize it and enable it to be eliminated from the body by other immune cells before signs of disease develop. It has been estimated that antibodies which can recognize as many as 10,000 different antigens or foreign infectious agents are circulating the blood stream.

A vaccine works in a similar way in that an antigenic response is produced. However, instead of initially suffering the natural infection and risking illness in order to develop this protective immunity, vaccines create a similar protective immunity without generally exposing the body to a condition wherein an infection could occur.

Development of vaccines against both bacterial and viral diseases has been one of the major accomplishments in medicine over the past century. While effective vaccines have been developed for a large number of diseases, the need for development of safe and effective vaccines for a number of other diseases remain.

Several basic strategies are used to make vaccines. One strategy is directed toward preventing viral diseases by weakening or attenuating a virus so that the virus reproduces very poorly once inside the body. Measles, mumps, rubella (German measles) and chickenpox (varicella) vaccines are made this way. Whereas natural viruses usually cause disease by reproducing themselves many thousands of times, weakened vaccine viruses reproduce themselves approximately 20 times. Such a low rate of replication is generally not enough to cause disease. Although the preparation of live, attenuated infectious agents as vaccines will often provide improved immunologic reactivity, such methods do increase the risk that the vaccine itself will be the cause of infection, and that the attenuated organism will propagate and provide a reservoir for future infection. One or two doses of live "weakened" viruses may provide immunity that is life-long; however, such vaccines cannot be given to people with weakened immune systems.

Another way to make viral vaccines is to inactivate the virus. By this method, viruses are completely inactivated or killed using a chemical. Killing the virus makes the virus unable to replicate in a body and cause disease. Polio, hepatitis A, influenza and rabies vaccines are made this way. The use of inactivated or killed bacterial or viral agents as a vaccine used to induce an antigenic response, although generally safe, will not always be effective if the antigenic characteristics of the agent are altered. An inactive virus can be given to people with weakened immune systems, but must be given multiple times to achieve immunity.

Vaccines may also be made using parts of a virus or bacteria. With this strategy, a portion of the virus is removed and used as a vaccine. The body is able to recognize the whole virus based on initial exposure to a portion of the virus. The hepatitis B vaccine for example, is composed of a peptide that resides on the surface of the hepatitis B virus.

Thus, one must generally choose between improved effectiveness and greater degree of safety when selecting between the inactivation and attenuation techniques for vaccine preparation. The choice is particularly difficult when the infectious agent is resistant to inactivation and requires highly rigorous inactivation conditions which are likely to degrade the antigenic characteristics which help to induce an immune response and provide subsequent immunity.

In addition to the dead or weakened infectious agent, vaccines usually contain sterile water or saline. Some vaccines are prepared with a preservative or antibiotic to prevent bacterial growth. Vaccines may also be prepared with stabilizers to help the vaccine maintain its effectiveness during storage. Other components may include an adjuvant which helps stimulate the production of antibodies against the vaccine to make it more effective.

Methods to prepare vaccines today involve treating samples with glutaraldehyde or formaldehyde to fix or cross-link the cells or infectious particles. Such treatments generally involve denaturation of the native forms of the infectious particles. A disadvantage to this approach is that the peptide coats of the infectious particles are damaged by this process, and thus may not be recognized by the immune system.

Many of the recent vaccine candidates are based on protected antigens, which are inherently less antigenic than the whole cell inactivated or live attenuated vaccines that were developed in the past. The challenge of formulating vaccines using these protected antigens is ensuring a sufficient immune response in vivo to convey immunity to the desired disease state. One manner in which this can be achieved is the discovery and development of novel adjuvants.

The goal of vaccination is to generate a strong immune response to the administered antigen, one that enables long-term protection against infection. This immune response can be enhanced by adding certain substances to the vaccines. These substances are called adjuvants, from the Latin adjuvare, which means to aid or help. Adjuvants can be used for various purposes. They can act to enhance the antigenicity of highly purified or recombinant antigens, they can reduce the amount of antigens or the number of immunizations needed for protective immunity, they can improve the efficacy of vaccines in newborns, elderly, or other immune-compromised persons, or they can act as antigen delivery systems for the uptake of antigens by mucosa. The chemical nature of adjuvants, their mechanism of action and their side effects are highly variable. Some of these side effects can be ascribed to an undesired stimulation of different mechanisms of the immune system, where others may reflect general adverse pharmacological reactions. There are many types of adjuvants. The most common adjuvants for human use are aluminum hydroxide, aluminum phosphate and calcium phosphate. There are also a number of adjuvants based on oil emulsions, products from bacterial (or their synthetic derivatives), endotoxins, fatty acids, paraffinic or vegetable oils, cholesterols, and aliphatic amines.

Aluminum salts, usually aluminum phosphate or aluminum hydroxide have been the most widely used adjuvants for human vaccines. Unfortunately, aluminum salts rarely induct cellular immune response and are generally relatively weak adjuvants. While the mechanism of action of aluminum salts is unknown, studies have suggested that they work by causing the formation of an antigen depot at the inoculation site from where the antigen is then slowly released. The immobilization of soluble antigens in the aluminum gel may also increase the duration of antigen interaction with the immune system. Other possible mechanisms of action involve complement, eosinophil and macrophage activation or an increased efficiency of antigen uptake by antigen presenting cells with a specific particulate matter size.

While aluminum salts have a relatively low rate of adverse effects, granulomas are common when the subcutaneous or intradermal injection route is used as opposed to intramuscular injection. Other limitations of aluminum adjuvants are increased IgE production, neurotoxicity and allergenicity. While under normal circumstances, small amounts of aluminum are excreted by the renal system, in situations of reduced kidney function, aluminum may accumulate in the body where it becomes highly toxic. In addition to aluminum salts, zirconium, iron and calcium salts have also been used to adsorb antigens. In particular, calcium salts have been used for diphtheria-tetanus-pertussis vaccines.

Adjuvant emulsions include oil in water or water in oil emulsions such as Freund's incomplete adjuvant (FIA), Montanide™, Adjuvant 65, and Lipovant™. These adjuvants work by forming a depot at the site of injection, enabling the meted release of antigenic material and the stimulation of antibody producing plasma cells. However, these adjuvants are have been deemed too toxic for widespread human prophylactic vaccine use and are usually reserved for those severe and/or terminal conditions such as cancer where there is a higher tolerance of side-effects.

Due to their potent immune-stimulatory capacity, bacteria-derived adjuvants are a major potential source of adjuvants. Lipopolysaccharide of Gram-negative bacteria or cell wall peptidoglycan enhances the immune response to co-administered antigenic material despite not being very antigenic themselves. This immune-stimulatory capacity works through the activation of toll-like receptors that activate the danger signals of the host immune system. Unfortunately, as killed or whole alive microorganisms these too are too toxic for widespread use in human prophylactic vaccines.

Problems with existing vaccines include at least the risks associated with adverse side effects, high cost, instability of the compound and/or its immunogenicity, the onset of an undesired disease state, and the spread of communicable potentially infectious agents. Thus, a clear need exists for a method of producing a vaccine for worldwide consumption with reduced risks of contamination, reliable stability and immunogenicity of the antigenic material, and an overall reduced quantity of antigenic material having the same or an equivalent efficacy as those currently available. In particular, there is demand for a safe and non-toxic adjuvant to stimulate cellular immunity.

SUMMARY OF THE INVENTION

The present invention overcomes problems associated with current vaccine production by providing a new method of increasing the efficacy of a vaccine with reduced expense and amount of antigenic material by incorporating a material to increase the body's immune response to the vaccine.

One embodiment of the invention is directed to a method of generating a protective immune response in a mammal that is protective against infection of a pathogen, comprising administering to said mammal a dose of an antigenic material and a peptide containing a sequence that comprises at least 12 contiguous amino acids of the sequence of PsaA. Preferably the amount of antigenic material per dose comprises one half, one quarter, or less of the amount of only antigenic material needed to generate a protective immune response in said mammal Preferably the amount of peptide is from about 0.1 to 10.0 micrograms per antigen unit, more preferably from about 0.5 to 5.0 micrograms per antigen unit, and more preferably from about 1.0 to 2.0 micrograms per antigen unit. Preferably the sequence comprises at least the sequence of SEQ ID NOs 1, 2 and/or 3, at least 18 contiguous amino acids of the sequence of SEQ ID NOs 1, 2 and/or 3, and/or the sequence of SEQ ID NOs 1, 2 and/or 3 with one or more conservative deletions, additions and/or substitutions. Also preferably, the antigenic material and the peptide are added together forming a mixture prior to administering to said mammal Preferably the mixture further comprises a pharmaceutically acceptable carrier or excipient, and/or a pharmaceutically acceptable preservative such as, for example, 2-phenoxyethanol, and/or a pharmaceutically acceptable inactivating agent such as, for example, formaldehyde, glutaraldehyde, beta propiolactone or a combination thereof. Preferably the pathogen is the etiological agent of cholera, pertussis, plague, typhoid, meningitis, Pneumococcal pneumonia, H. influenza type B, leprosy, gonorrhea, meningococcus, sepsis, *Pseudomonas aeruginosa*, diphtheria, botulism, tetanus, poliomyelitis, measles, rubella, yellow fever, mumps, hepatitis B, hepatitis C, influenza, adenovirus, anthrax, human papilloma virus, rabies, rotavirus, varicella, shingles, or a combination thereof.

Another embodiment of the invention is directed to a method of generating an immune response in a patient that is protective against infection by a pathogen comprising administering to said mammal a dose of an antigenic material and a peptide containing a sequence that comprises one or more epitopes of the sequence of PsaA, SEQ ID NOs 1, 2 and/or 3, epitopes thereof, variations and derivatives thereof, and/or the sequence of any of the foregoing with one or more conservative amino acid deletions, additions or substitutions. Preferably, presence of the peptide reduces the amount of antigenic material needed to produce a protective immune response by at least half as compared to a vaccine of only antigenic material. Also preferably, the adjuvant comprises all or at least 8, 12, or 16 contiguous amino acids of the sequence of SEQ ID NOs 1, 2 or 3, epitopes thereof, and with one or more conservative deletions, additions and/or amino acid substitutions. Preferably, the amount of antigenic material comprises from about 0.1 to about 0.5 antigenic units per individual dose, or about one tenth to about one half of the amount of antigenic material of a vaccine containing no adjuvant. Preferably the amount of the peptide comprises from 0.5 to 10.0 micrograms per individual dose and the peptide comprises the sequence of SEQ ID NO 1 or 2. Preferably, the antigenic material, when administered to a mammal, generates and immune response against polio, measles, mumps, rubella or chickenpox.

Another embodiment of the invention is directed to a vaccine or adjuvant composition comprising an antigenic material and an adjuvant comprising PsaA protein and/or derivatives and variants thereof; SEQ ID NOs 1, 2 or 3; 2 4, 6, 8, 10, 12, 14, 16, 18, or more contiguous amino acids of the sequence of PsaA or SEQ ID NOs 1, 2 or 3; epitopes of any of the foregoing, and/or one or more conservative, additions, deletions and/or substitutions thereof and preferably further comprising a pharmaceutically acceptable carrier or excipient.

Another embodiment of the invention is directed to nucleic acid sequences and vectors that encode PsaA protein and derivatives and variants thereof; SEQ ID NOs 1, 2 or 3; 4, 6, 8, 10, 12, 14, 16, 18, 20, 22 or more contiguous amino acids of the sequence of SEQ ID NOs 1, 2 or 3; epitopes of any of the foregoing; and/or one or more conservative, additions, deletions and/or substitutions thereof, and further comprising a pharmaceutically acceptable carrier or excipient.

Other embodiments and advantages of the invention are set forth in part in the description, which follows, and in part, may be obvious from this description, or may be learned from the practice of the invention.

DESCRIPTION OF THE INVENTION

The production of vaccines is the most important route of preventing and treating viral infections. Although a plethora of antiviral agents are available, science has yet to discover antiviral agents that combat each viral agent. While administering antibodies can combat certain disease states, prophylaxis through active immunization continues to be the most efficacious and safe way of dealing with viral infections. The addition of secondary agents to increase the immune response to an antigenic material introduced to the body is critical to providing long-term protection against infection when utilizing killed as opposed to live attenuated vaccines. Adjuvant activity is manifested by a significant increase in immune-mediated protection by development of an immune response in an individual who otherwise would not respond to a particular vaccine.

It has been surprisingly discovered that the addition of peptides derived from pneumococcal surface adhesin A protein to a vaccine formulation increases the in vivo immune response such that a lower dose of antigenic material is required to produce a protective neutralizing antibody titer. Pneumococcal surface adhesin A (PsaA) is a surface-exposed common 37-kilodalton multi-functional lipoprotein detected on all known serotypes of *Streptococcus pneumoniae*. Different serotypes of *S. pneumoniae* contain conservative variations and derivatives of PsaA. This lipoprotein belongs to the ABC-type transport protein complex that transports manganese across membranes. PsaA is an adhesin molecule that has a significant role in attachment to host cells and also virulence. PsaA is immunogenic and elicits an increase in antibody response against PsaA in an exposed animal. The invention provides a method for enhancing the immune response of a mammal to a vaccine comprising administering to a mammal in need of vaccination an effective amount of peptides derived from PsaA in conjunction with an antigenic material. Thus, the invention provides a less expensive method of producing vaccines with the same or greater efficacy as those currently available using a dose reduction agent. The total amount of antigenic material needed to develop an immunological response is reduced such that the final per dose cost of the vaccine is affordable for both developed and underdeveloped countries. The resulting vaccine is safe and effective, without inducing a disease state, adverse side effects, or the risk of spreading communicable conditions.

The amount of antigenic material needed per dose of vaccine without adjuvant, in other words the amount needed to generate a protective immune response in the patient (also referred to herein as the pharmaceutically acceptable amount of only antigenic material), is reduced to a surprising amount when the adjuvant of the invention is included. Preferably, the amount of antigenic material per dose of vaccine plus adjuvant of the invention is about one tenth or less of the amount required when administering antigenic material without adjuvant of the invention, more preferably about one quarter or less, more preferably about one third or less, more preferably about one half or less, more preferably about two thirds or less, or more preferably about three quarters or less. The amount of peptide per dose needed is from about 0.5 to 50 micrograms, more preferably from about 1.0 to 20.0 micrograms, and more preferably from about 2.0 to 10.0 micrograms. Preferably, the antigenic material of the vaccine and the adjuvant material of the invention are mixed prior to administration to the patient. The composition may include one or more pharmaceutically acceptable carriers, excipients, preservatives and/or inactivating agents. Preferred carriers include, for example, one or more of salts, buffers, fatty acids, detergents, surfactants, anti-foaming agents, carbohydrates, and/or glycerol. One preferred preservative is 2-phenoxyethanol and preferred inactivating agents include, for example, glutaraldehyde, formamide, formaldehyde, beta propiolactone and combinations thereof.

The methods of the invention are effective for enhancing primary immune responses in mammals to antigenic material present in a vaccine, thereby enhancing an effective level of antibodies in mammals exposed to antigenic material in vaccines and enhancing a primary immune response wherein the immune response by the mammal without the administration of peptides derived from PsaA would not be strong enough to prevent disease. One result of this discovery is that more doses can be made from the same amount of antigenic material. In turn this reduces the cost of preparing the unit dose of the vaccine. Vaccines of the invention also produce a greater antibody response as evidenced at least by a higher resulting titer as compared to the resulting title after administration of only antigenic material.

Preferred antigenic material includes, for example, antigenic material that is immunogenic for development of bacterial vaccines, toxoid vaccines and viral vaccines, or mixtures thereof and preferably for immunization. Preferred vaccines include, for example, vaccines for treatment against infections of cholera, pertussis, plague, typhoid, meningitis, pneumococcal pneumonia, H. influenza type B, leprosy, gonorrhea, meningococcus, sepsis, *pseudomonas aeruginosa*, diphtheria, botulism, tetanus, poliomyelitis, measles, rubella, yellow fever, mumps, hepatitis B, hepatitis C, influenza, adenovirus, anthrax, human papilloma virus, rabies, rotavirus, varicella, shingles, other disease states for which vaccination is available, and combinations thereof.

Preferably, vaccines are developed from antigenic material administered in conjunction with an adjuvant that comprises a sequence derived from PsaA. The invention includes adjuvants directed to PsaA protein sequences (SEQ ID NO 3) and also conservative deletions or additions or non-deleterious amino acid substitutions, for example of one or more epitopes of PsaA as predicted by P. C. Ng and Steven Henikoff (*Genome Res.* 11:863-874 (2001)). The sequences of the peptide adjuvants of the present invention are derived from one or more of a plurality of contiguous amino acids of PsaA, and/or sequences that represent epitopes or antigenic regions of adhesion A. More preferably such sequences are or are derived from all or part of the sequence of SEQ ID NO 1. Preferably, the plurality comprises at least 6 contiguous amino acids of adhesion A or SEQ ID NOs 1, 2 or 3, more preferably at least 8 contiguous amino acids, more preferably at least 10 contiguous amino acids, more preferably at least 12 contiguous amino acids, more preferably at least 14 contiguous amino acids, more preferably at least 16 contiguous amino acids, more preferably at least 18 contiguous amino acids, more preferably at least 20 contiguous amino acids, more preferably at least 22 contiguous amino acids, more preferably at least 24 contiguous amino acids, more preferably at least 26 contiguous amino acids, and more preferably the complete sequence of adhesion A or SEQ ID NOs 1, 2 or 3. Peptides of SEQ ID NO 1 were originally developed to inhibit the internalization of *Streptococcus pneumonia* by nasopharyngeal cells (US2008/0305123; WO2006/127020). These peptides were shown to activate various cell lines and increase the opsonophagocytosis capabilities of host cells in vitro (WO2010/014888). Peptides of the invention preferably contain only the functional epitopes of the PsaA peptide of *Streptococcus pneumonia*. The peptides of the invention can be synthesized by means of standard and modified 9-fluorenylmethoxycarbonyl protocols. The lyophilized peptides can then be resuspended in diethylpyrocarbonate water, sonicated for 3 minutes for dissolution, and stored for later use.

Many vaccine formulations benefit from the use of excipients, carriers, viral inactivators, preservatives, antimicrobial compounds, sterile water, stabilizers, pH adjustors, detoxifiers, lubricants, antifoaming agents, and surfactants. These include ammonium sulfate, alphotericin B, ascorbic acid, bactopeptone, beta-propiolactone, benzethonium chloride, bovine albumin, bovine serum, chlortetracycline, ethylenediamine-tetraacetic acid sodium (EDTA), fetuin, formaldehyde, gelatin, gentamicin, glycine, glycerin, human serum albumin, hydrochloric acid, hydrogen peroxide, kanamycin, lactose, magnesium stearate, monosodium glutamate, neomycin, ovalbumin, phenol, phenol red, 2-phenoxyethanol, phosphate buffers (disodium, monosodium, potassium, sodium dihydrogen phosphate), polydimethylsilozone, polyethylene glycol p-isocytl-phenyl ether, polymyxin B, polyoxyethylene 9-10 nonyl phenol, polysorbate 20, polysorbate 80, potassium glutamate, silicon, sodium acetate, sodium bisulfate, sodium borate, sodium chloride, sodium hydroxide, sorbitol, streptomycin, sucrose, thimerosal, tur(n)butyl-phosphate. Other pharmaceutically acceptable carriers may be used that are well known to those skilled in the art.

Another embodiment of the invention comprises compositions comprising antigenic material and/or adjuvant comprising peptides containing sequences derived from all or parts of PsaA, epitopes of PsaA, or PsaA with one or more conservative deletions, additions or substitutions of the sequence of all or portions of PsaA or SEQ ID NOs 1, 2 or 3, and compositions of only adjuvant peptides of the invention. Compositions may be aqueous or non-aqueous and maintained in saline, water, fatty acids, carbohydrates or oils and maintained at ambient temperature, refrigerated or frozen. Compositions of the invention may be maintained as a solid and preferably dry such as, for example, lyophilized powder. Preferably dry compositions are packaged for transport and storage and packages contain instructions for rehydration and administering to patients.

Another embodiment of the invention is directed to nucleic acid sequences and vectors that encode peptides containing sequences derived from all or parts of PsaA or SEQ ID NOs 1, 2 or 3; derivatives and serotype variations thereof; epitopes thereof; or one or more conservative deletions, additions or substitutions of any of the foregoing.

The following examples illustrate embodiments of the invention, but should not be viewed as limiting the scope of the invention.

EXAMPLES

Example 1 28 Dose Preparation of Inactivated Polio Vaccine Formulation Using ½ the Standard IPV Dose Inactivated polio vaccine vial containing 40 D-antigen units of poliomyelitis virus type 1, Mahoney strain, 8 D-antigen units of poliomyelitis virus type 2, MED-I strain and 32 D-antigen units of poliomyelitis virus type 3, Saukett strain was unpacked and pooled in a separate sterile container (Falcon). An antigen unit is the smallest amount of antigen that, in the presence of specific antiserum, will bind to one complement unit. A D-antigen unit is a unit of potency of vaccine typically used for poliomyelitis prevention. 7 mL IPV was withdrawn into a separate sterile container. Peptides derived from PsaA stock (1 mg/mL) was prepared by dissolving 10 mg of the peptide in 10 mL of WFI. 2-phenoxyethanol (5 mg/mL) and formaldehyde (25 mcg/mL) were dissolved in a PBS buffer. The peptide and the 2-pheoxyethanol and formaldehyde solutions are then mixed together and filtered through a 0.2 micron sterile filter. The 7 mL IPV and 7 mL of the solution containing the peptide, formaldehyde and 2-phenoxyethanol were pooled together. The total volume prepared is 14 mL, consisting of 7 mL inactivated polio vaccine and 7 mL of the peptide, 2-phenoxyethanol and formaldehyde mixture. This volume makes 28, 0.5 mL polio vaccine doses.

Example 2 28 Dose Preparation of Inactivated Polio Vaccine Formulation Using ¼ the Standard IPV Dose Inactivated polio vaccine vial containing 40 D-antigen units of poliomyelitis virus type 1, Mahoney strain, 8 D-antigen units of poliomyelitis virus type 2, MED-I strain and 32 D-antigen units of poliomyelitis virus type 3, Saukett strain was unpacked and pooled in a separate sterile container (Falcon). 3.5 mL IPV was withdrawn into a separate sterile container. Peptides derived from PsaA stock (1 mg/mL) was prepared by dissolving 10 mg of the peptide in 10 mL of WFI. 2-phenoxyethanol (5 mg/mL) and formaldehyde (25 mcg/mL) were dissolved in a PBS buffer. The peptide and the 2-pheoxyethanol and formaldehyde solutions are then mixed together and filtered through a 0.2 micron sterile filter. The 3.5 mL IPV and 10.5 mL of the solution containing the peptide, formaldehyde and 2-phenoxyethanol were pooled together. The total volume prepared is 14 mL, consisting of 7 mL inactivated polio vaccine and 7 mL of the peptide, 2-phenoxyethanol and formaldehyde mixture. This volume makes 28, 0.5 mL polio vaccine doses.

Example 3 28 Dose Preparation of Inactivated Polio Vaccine Formulation Using ⅛$^{th}$ the Standard IPV Dose Inactivated polio vaccine vial containing 40 D-antigen units of poliomyelitis virus type 1, Mahoney strain, 8 D-antigen units of poliomyelitis virus type 2, MED-I strain and 32 D-antigen units of poliomyelitis virus type 3, saukett strain was unpacked and pooled in a separate sterile container (Falcon). 1.75 mL IPV was withdrawn into a separate sterile container. Peptides derived from PsaA stock (1 mg/mL) was prepared by dissolving 10 mg of the peptide in 10 mL of WFI. 2-phenoxyethanol (5 mg/mL) and formaldehyde (25 mcg/mL) were dissolved in a PBS buffer. The peptide and the 2-pheoxyethanol and formaldehyde solutions are then mixed together and filtered through a 0.2 micron sterile filter. The 1.75 mL IPV and 13.25 mL of the solution containing the peptide, formaldehyde and 2-phenoxyethanol were pooled together. The total volume prepared is 14 mL, consisting of 7 mL inactivated polio vaccine and 7 mL of the peptide, 2-phenoxyethanol and formaldehyde mixture. This volume makes 28, 0.5 mL polio vaccine doses.

These examples show that it is possible to design an effective vaccine utilizing only a fraction of the antigenic materials thought to be the minimum amount possible to confer lasting immunity. These novel vaccine formulations advantageously significantly reduce the per dose cost of producing the desired vaccine.

Sequence Information

```
                                           SEQ ID NO 1
    LFVESSVRRP MKTVSQDTNI PIYAQIF (27 aa's)

SEQ ID NO 2
    LFVESSVDDR PMKTVSQDTN IPIYAQIF (28 aa's)

SEQ ID NO 3:
    MKKLGTLLVL FLSAIILVAC ASGKKDTTSG QKLKVVATNS
    IIADITKNIA GDKIDLHSIV PIGQDPHEYE PLPEDVKKTS
    EADLIFYNGI NLETGGNAWF TKLVENAKKT ENKDYFAVSD
    GVDVIYLEGQ NEKGKEDPHA WLNLENGIIF AKNIAKQLSA
    KDPNNKEFYE KNLKEYTDKL DKLDKESKDK FNKIPAEKKL
    IVTSEGAFKY FSKAYGVPSA YIWEINTEEE GTPEQIKTLV
    EKLRQTKVPS LFVESSVDDR PMKTVSQDTN IPIYAQIFTD
    SIAEQGKEGD SYYSMMKYNL DKIAEGLAK
```

(309 Amino Acid Sequence of PsaA of *Streptococcus pneumoniae*)

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. The term comprising, where ever used, is intended to include the terms consisting and consisting essentially of. Furthermore, the terms comprising, including, and containing are not intended to be limiting. It is intended that the specification and examples be considered exemplary only with the true scope and spirit of the invention indicated by the following claims.

The invention claimed is:

1. A method of generating a protective immune response in a mammal that is protective against infection by a polio virus, comprising administering to said mammal a composition comprising a dose of an antigenic material that generates an immune response to the polio virus and an adjuvant comprising a pneumococcal peptide containing a sequence that comprises SEQ ID NO 1, SEQ ID NO 2 or SEQ ID NO 3; wherein said pneumococcal peptide increases the immune response to the polio virus; and wherein said composition does not comprise other pneumococcal antigenic material.

2. The method of claim 1, wherein the amount of antigenic material per dose comprises one quarter or less of the amount of only antigenic material needed to generate a protective immune response in said mammal.

3. The method of claim 1, wherein the amount of antigenic material per dose comprises one half or less of the amount of only antigenic material needed to generate the protective immune response in said mammal.

4. The method of claim 1, wherein the amount of peptide per dose is from about 0.1 to 10.0 micrograms per antigen unit.

5. The method of claim 1, wherein the amount of peptide per dose is from about 0.5 to 5.0 micrograms per antigen unit.

6. The method of claim 1, wherein the amount of peptide per dose is from about 1.0 to 2.0 micrograms per antigen unit.

7. The method of claim 1, wherein the sequence comprises at least the sequence of SEQ ID NO 1 or SEQ ID NO 2.

8. The method of claim 1, wherein the antigenic material and the peptide are added together and form a mixture prior to administering to said mammal.

9. The method of claim 8, wherein the mixture further comprises a pharmaceutically acceptable carrier or excipient.

10. The method of claim 8, wherein the mixture further comprises a pharmaceutically acceptable preservative.

11. The method of claim 10, wherein the pharmaceutically acceptable preservative is 2-phenoxyethanol.

12. The method of claim 8, wherein the mixture further comprises a pharmaceutically acceptable inactivating agent.

13. The method of claim 12, wherein the pharmaceutically acceptable inactivating agent is formaldehyde, glutaraldehyde, beta propiolactone or a combination thereof.

14. The method of claim 1, wherein the peptide acts as an adjuvant and reduces the amount of antigenic material needed to produce a protective immune response by at least half as compared to a vaccine of only antigenic material.

15. The method of claim 1, wherein the antigenic material comprises attenuated or inactivated poliomyelitis virus type 1, poliomyelitis virus type 2, poliomyelitis virus type 3, or a combination thereof.

16. The method of claim 1, wherein the antigenic material comprises a type 1 poliomyelitis virus strain.

17. The method of claim 16, wherein the type 1 strain is a Mahoney strain.

18. The method of claim 1, wherein the antigenic material comprises a type 2 poliomyelitis virus strain.

19. The method of claim 18, wherein the type 2 strain is a MEF-1 strain.

20. The method of claim 1, wherein the antigenic material comprises a type 3 poliomyelitis virus strain.

21. The method of claim 20, wherein the type 3 strain is a Saukett strain.

22. The method of claim 1, wherein the antigenic material is selected from the group consisting of poliomyelitis virus type 1 Mahoney strain, poliomyelitis virus type 2 MEF-1 strain, poliomyelitis virus type 3 Saukett strain and combinations thereof.

* * * * *

SEQUENCE LISTING

<160> NUMBER OF SEQ ID NOS: 3

<210> SEQ ID NO 1
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Leu Phe Val Glu Ser Ser Val Arg Arg Pro Met Lys Thr Val Ser Gln
1               5                   10                  15

Asp Thr Asn Ile Pro Ile Tyr Ala Gln Ile Phe
            20                  25

<210> SEQ ID NO 2
<211> LENGTH: 28
<212> TYPE: PRT
<213> ORGANISM: Streptococcus pneumoniae

<400> SEQUENCE: 2

Leu Phe Val Glu Ser Ser Val Asp Asp Arg Pro Met Lys Thr Val Ser
1               5                   10                  15

Gln Asp Thr Asn Ile Pro Ile Tyr Ala Gln Ile Phe
            20                  25

<210> SEQ ID NO 3
<211> LENGTH: 309
<212> TYPE: PRT
<213> ORGANISM: Streptococcus pneumoniae

<400> SEQUENCE: 3

Met Lys Lys Leu Gly Thr Leu Leu Val Leu Phe Leu Ser Ala Ile Ile
1               5                   10                  15

Leu Val Ala Cys Ala Ser Gly Lys Lys Asp Thr Thr Ser Gly Gln Lys
            20                  25                  30

Leu Lys Val Val Ala Thr Asn Ser Ile Ile Ala Asp Ile Thr Lys Asn
        35                  40                  45

Ile Ala Gly Asp Lys Ile Asp Leu His Ser Ile Val Pro Ile Gly Gln
50                  55                  60

Asp Pro His Glu Tyr Glu Pro Leu Pro Glu Asp Val Lys Lys Thr Ser
65                  70                  75                  80

Glu Ala Asp Leu Ile Phe Tyr Asn Gly Ile Asn Leu Glu Thr Gly Gly
                85                  90                  95

Asn Ala Trp Phe Thr Lys Leu Val Glu Asn Ala Lys Lys Thr Glu Asn
            100                 105                 110

Lys Asp Tyr Phe Ala Val Ser Asp Gly Val Asp Val Ile Tyr Leu Glu
        115                 120                 125

Gly Gln Asn Glu Lys Gly Lys Glu Asp Pro His Ala Trp Leu Asn Leu
130                 135                 140

Glu Asn Gly Ile Ile Phe Ala Lys Asn Ile Ala Lys Gln Leu Ser Ala
145                 150                 155                 160

Lys Asp Pro Asn Asn Lys Glu Phe Tyr Glu Lys Asn Leu Lys Glu Tyr
                165                 170                 175

Thr Asp Lys Leu Asp Lys Leu Asp Lys Glu Ser Lys Asp Lys Phe Asn
            180                 185                 190

Lys Ile Pro Ala Glu Lys Lys Leu Ile Val Thr Ser Glu Gly Ala Phe
        195                 200                 205

```
Lys Tyr Phe Ser Lys Ala Tyr Gly Val Pro Ser Ala Tyr Ile Trp Glu
    210             215                 220

Ile Asn Thr Glu Glu Glu Gly Thr Pro Glu Gln Ile Lys Thr Leu Val
225             230                 235                 240

Glu Lys Leu Arg Gln Thr Lys Val Pro Ser Leu Phe Val Glu Ser Ser
            245                 250                 255

Val Asp Asp Arg Pro Met Lys Thr Val Ser Gln Asp Thr Asn Ile Pro
            260                 265                 270

Ile Tyr Ala Gln Ile Phe Thr Asp Ser Ile Ala Glu Gln Gly Lys Glu
        275             280                 285

Gly Asp Ser Tyr Tyr Ser Met Met Lys Tyr Asn Leu Asp Lys Ile Ala
        290             295                 300

Glu Gly Leu Ala Lys
305
```